US00PP20291P3

(12) United States Plant Patent
Ackerman et al.

(10) Patent No.: US PP20,291 P3
(45) Date of Patent: Sep. 15, 2009

(54) STRAWBERRY PLANT NAMED 'PS-5096'

(50) Latin Name: *Fragaria ananassa*
Varietal Denomination: PS-5096

(75) Inventors: Stephen M. Ackerman, Salinas, CA (US); Steven D. Nelson, Watsonville, CA (US); Michael D. Nelson, Watsonville, CA (US)

(73) Assignees: Plant Sciences, Inc., Watsonville, CA (US); Berry R&D, Inc., Watsonville, CA (US)

( * ) Notice: Subject to any disclaimer, the term of this patent is extended or adjusted under 35 U.S.C. 154(b) by 164 days.

(21) Appl. No.: 11/730,332

(22) Filed: Mar. 30, 2007

(65) Prior Publication Data

US 2008/0141405 P1 Jun. 12, 2008

Related U.S. Application Data

(60) Provisional application No. 60/852,999, filed on Oct. 20, 2006.

(51) Int. Cl.
*A01H 5/00* (2006.01)

(52) U.S. Cl. ..... Plt./209

(58) Field of Classification Search ..... Plt./208, Plt./209

See application file for complete search history.

*Primary Examiner*—Howard J Locker
(74) *Attorney, Agent, or Firm*—Foley & Lardner LLP

(57) ABSTRACT

This invention relates to a new and distinct variety of strawberry plant named 'PS-5096'. This new strawberry plant named 'PS-5096' is primarily adapted to the growing conditions of the central coast of California, and is characterized by medium to small sized fruit which are orange-red to red in color; medium to small calyx diameter; conical, glossy fruit with the calyx which tends to be slightly reflexed; medium green foliage, which is slightly concave to slightly convex in shape with medium interveinal blistering and gloss; and position of fruiting truss tends to be more level with to above the plant with weak pubescence.

4 Drawing Sheets

Latin name of the genus and species of the plant claimed: *Fragaria ananassa.*
Variety denomination: 'PS-5096'.

BACKGROUND OF THE INVENTION

The present invention relates to a new and distinct strawberry variety designated as 'PS-5096'. This new variety is a result of a controlled cross made by the inventors Stephen M. Ackerman, Steven D. Nelson, and Michael D. Nelson, in 1997 between strawberry variety 'PS-592' (patented, U.S. Plant Pat. No. 9,903) and strawberry variety designated 'PS-1150' (patented, U.S. Plant Pat. No. 10,780). It is unknown as to which parent variety is the seed parent and which parent variety is the pollen parent. The variety is botanically known as *Fragaria ananassa.*

The seedling resulting from the aforementioned cross was asexually propagated by stolons in a nursery located in Siskiyou County, California, and was subsequently selected by the inventors from a controlled breeding plot in Salinas, Calif., in 1999. After its selection, the new variety was further asexually propagated by stolons in both Siskiyou County, California and San Joaquin County, California. The new variety was extensively tested over the next several years in fruiting fields of Salinas, Calif. This propagation has demonstrated that the combination of traits disclosed herein as characterizing the new variety are fixed and remain true to type through successive generations of asexual reproduction.

BRIEF SUMMARY OF THE INVENTION

'PS-5096' is primarily adapted to the climate and growing conditions of the central coast of California. This region provides the necessary winter temperatures required for it to produce a strong vigorous plant and to remain in fruit production from April through November. The nearby Pacific Ocean provides the needed humidity and moderate temperatures to maintain fruit quality during the spring and summer production months.

The following traits have been repeatedly observed and are determined to be unique characteristics of 'PS-5096', which in combination distinguish this strawberry plant as a new and distinct variety:

1. Medium to small sized fruit;
2. Orange-red to red fruit color;
3. Medium to small calyx diameter;
4. Conical, glossy fruit with the calyx which tends to be slightly reflexed;
5. Medium green foliage; slightly concave to slightly convex in shape with medium interveinal blistering and gloss; and
6. Position of fruiting truss tends to be more level with to above the plant with weak pubescence.

The strawberry varieties that are believed to be most closely related to the new strawberry variety 'PS-5096' are the parental cultivars, strawberry variety 'PS-592' (patented, U.S. Plant Pat. No. 9,903) and strawberry variety 'PS-1150' (patented, U.S. Plant Pat. No. 10,780).

In side-by-side comparisons to the similar strawberry varieties 'PS-592' and 'PS-1150', the new strawberry variety 'PS-5096' differs by the following combination of characteristics as described in Table 1:

TABLE 1

| Characteristic | 'PS-5096' | 'PS-592' (U.S. Plant Pat. No. 9,903) | 'PS-1150' (U.S. Plant Pat. No. 10,780) |
|---|---|---|---|
| 1. Average berry weight (gm) | 19.3 | 23.1 | 17.6 |
| 2. Achenes per berry | 254 | 304 | 293 |
| 3. Distribution of red color of the internal flesh | Only marginal | Marginal & central | Marginal & central |
| 4. Number of crowns per Plant | 5.5 | 5.0 | 5.0 |
| 5. Plant Size | Medium to large | Large | Medium |
| 6. Stolon anthocyanin intensity | Absent or very weak | Medium | Medium to strong |
| 7. Stolon pubescence | Weak to medium | Medium | Medium to strong |
| 8. Foliage Color (upper surface) | Medium green | Medium green | Medium green |
| 9. Foliage interveinal blistering | Medium | Medium to strong | Weak to medium |
| 10. Foliage gloss | Medium | Strong | Weak |
| 11. Fruiting truss position relative to foliage | Level with to above | Level with to beneath | Above |
| 12. Fruiting truss pubescence | Weak | Medium | Medium |

For identification a series of AFLP molecular markers have been determined for this new variety.

BRIEF DESCRIPTIONS OF THE DRAWINGS

The accompanying color photographs illustrate the overall appearance of typical specimens of the new strawberry variety 'PS-5096', at various stages of development as true as it is reasonably possible with color reproductions of this type. Color in the photographs may differ slightly from the color value cited in the botanical description which accurately describe the color of 'PS-5096'. The depicted plant and plant parts of the new strawberry variety 'PS-5096' were taken in Salinas, Calif., and are approximately 8 to 9 months old.

DETAILED BOTANICAL DESCRIPTION

Figure 1:
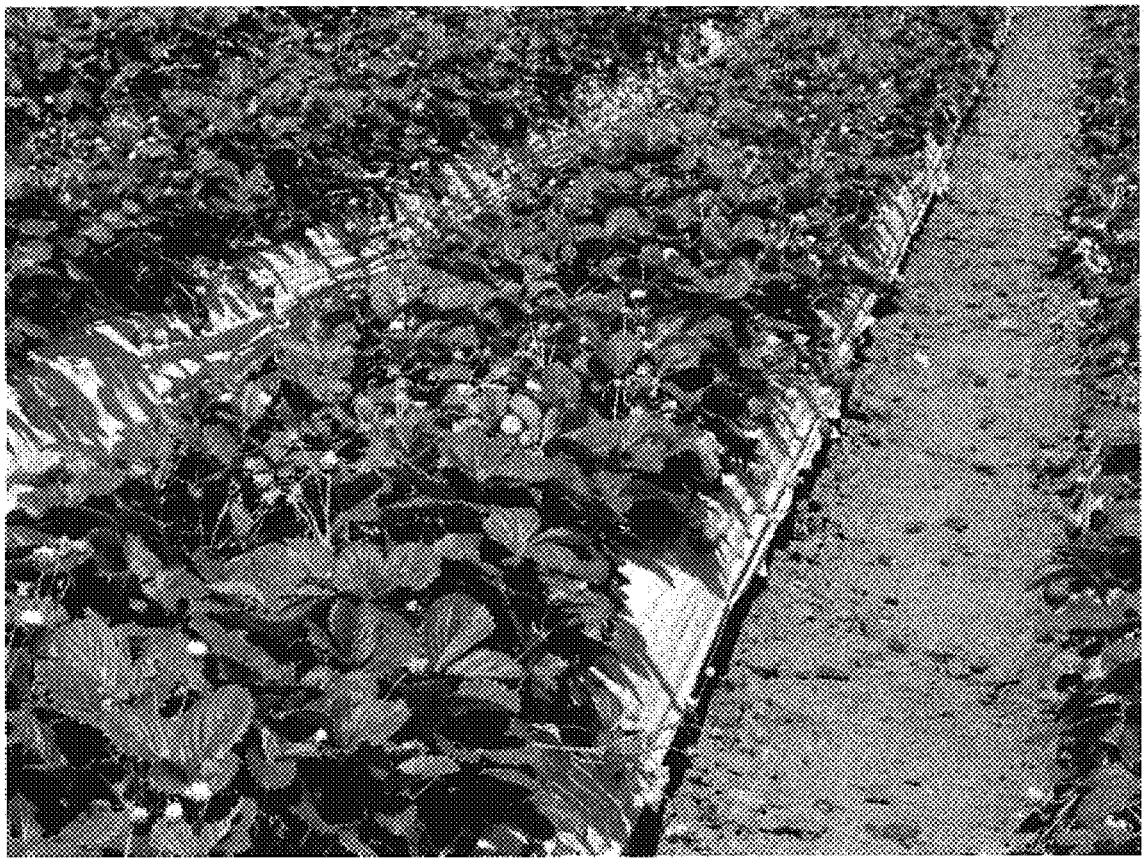
FIG. 1 shows typical fruiting field characteristics taken in the month of June, 2006.
Figure 2:
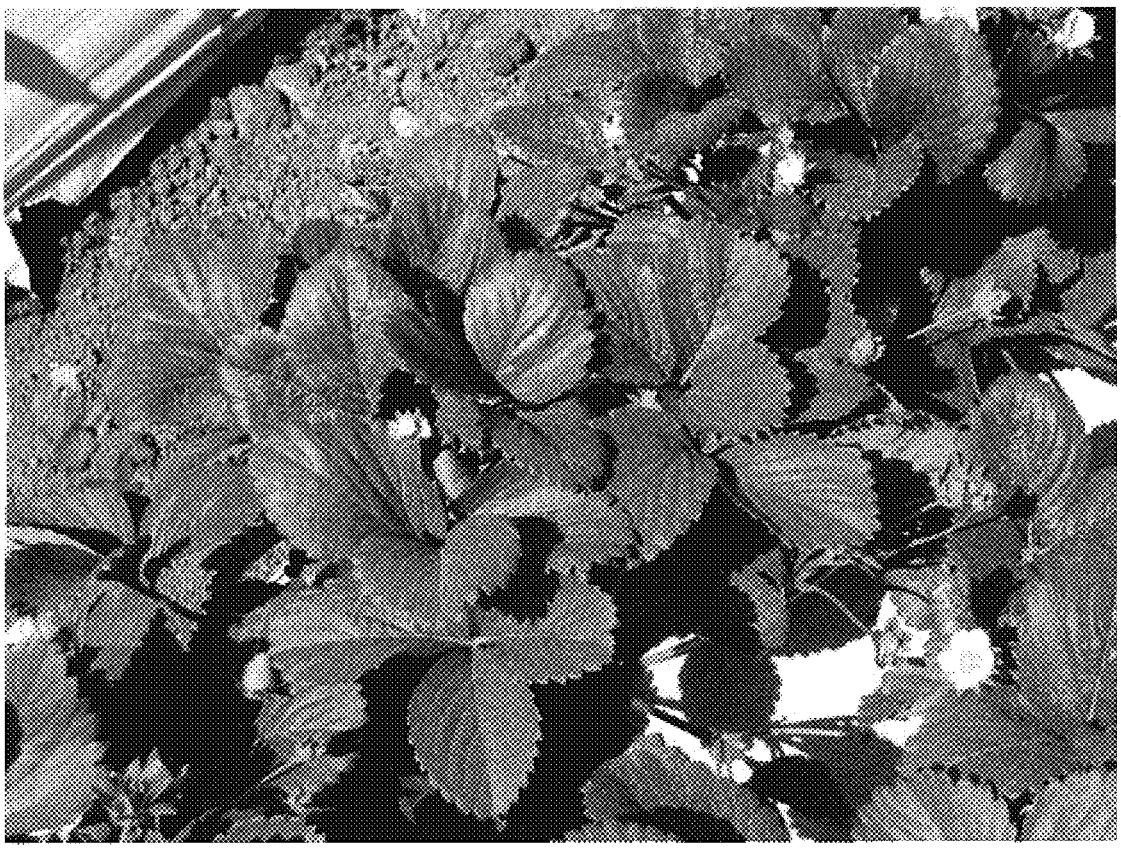
FIG. 2 shows a close-up view of typical leaf structure taken in the month of June, 2006.
Figure 3:
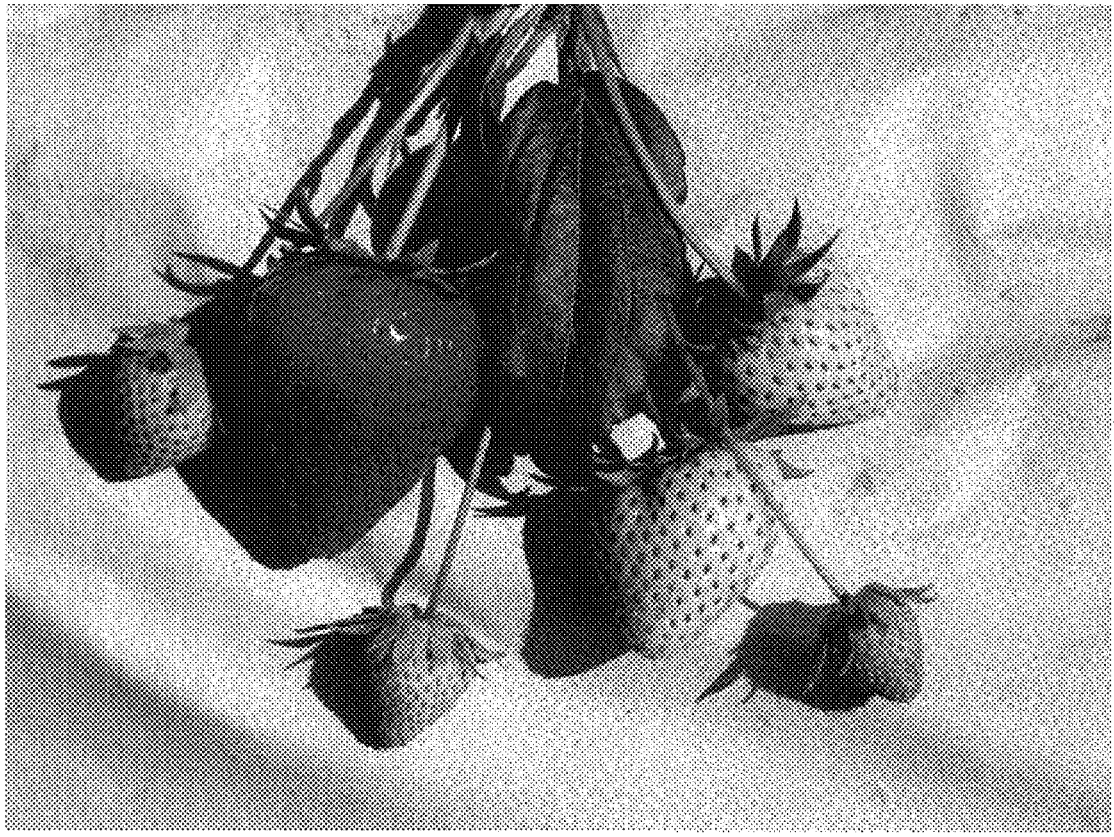
FIG. 3 shows typical mature and immature field fruit taken in the month of June, 2006.
Figure 4:
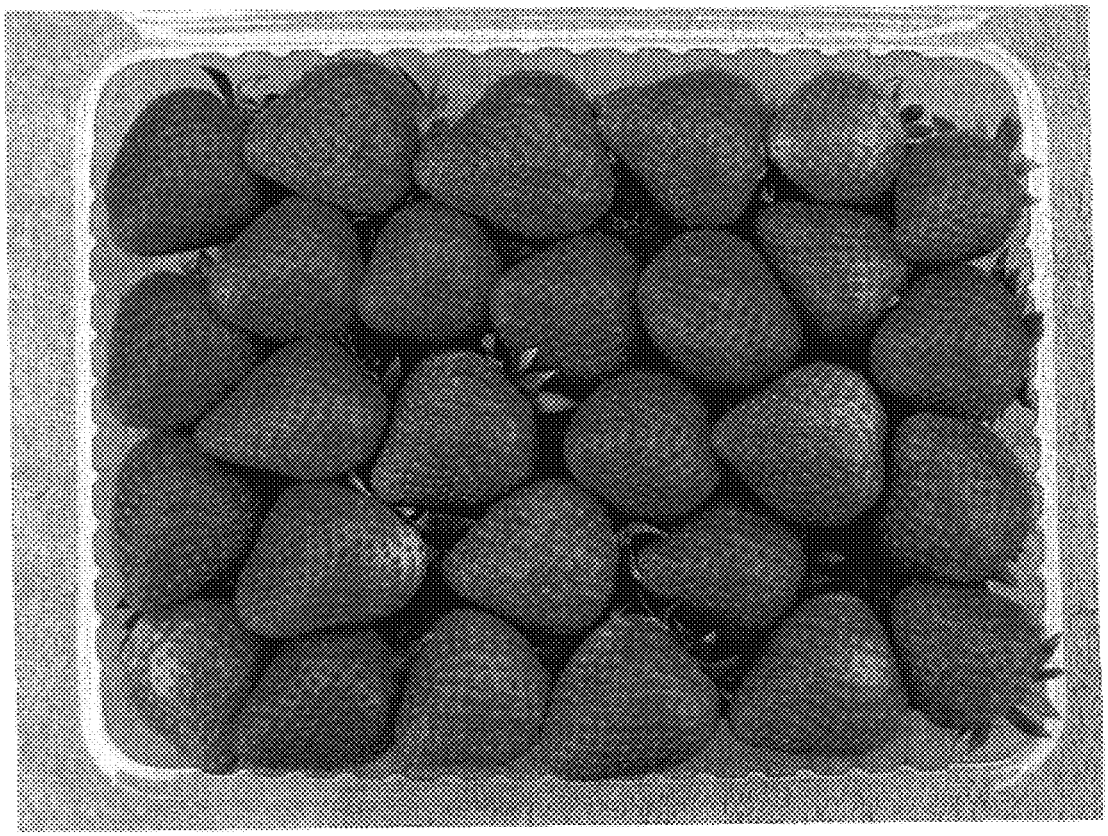
FIG. 4 shows a close-up view of fruit taken in the month of July, 2006.

'PS-5096' has not been observed under all possible environmental conditions. The characteristics of the new variety may vary in detail, depending upon variations in environmental factors, including weather (temperature, humidity and light intensity), day length, soil type and location.

The aforementioned photographs, together with the following description of the new variety 'PS-5096', unless otherwise noted, is based on observations taken during the 2006 growing season in Salinas, Calif. These measurements and ratings were taken from plants of 'PS-5096' dug from a high-elevation nursery located in Siskiyou County, California during the middle of October 2005 and planted approximately 3 weeks later in Salinas, Calif. The approximate age of the observed plants is 7 to 10 months. Yield observations and fruit quality characteristics are averaged from four years of data collected from the 2003 through 2006 growing seasons. Flower measurements and characteristics are from secondary flowers unless otherwise noted. Fruit characteristics and measurements are from secondary fruit unless otherwise noted.

Color terminology where noted follows the Munsell Book of Colors, Munsell Color, Baltimore, Md. (1976).

The following Tables 2–8 describe fruit, plant, stolon, foliage, fruiting truss, flower and pest/disease characteristics of the new strawberry 'PS-5096' in comparison to the similar strawberry varieties 'PS-592' and 'PS-1150'.

TABLE 2

FRUIT CHARACTERISTICS

| Characteristic | 'PS-5096' | 'PS-592' (U.S. Plant Pat. No. 9,903) | 'PS-1150' (U.S. Plant Pat. No. 10,780) |
|---|---|---|---|
| Color of mature fruit | 7.5R 3/12-4/12 Orange red to red | 7.5R 3/12-4/12 Orange red to red | 7.5R 4/10-3/8 Red |
| Color of internal flesh | 7.5R 4/10-4/12 Medium red | 7.5R 5/10-4/10 Light red | 7.5R 4/10-4/12 Medium red |
| Length (cm) | 4.39 | 4.83 | 4.20 |
| Width (cm) | 3.68 | 4.26 | 3.69 |
| Ratio length/width | 1.19 Slightly longer than broad | 1.13 Slightly longer than broad | 1.14 Slightly longer than broad |
| Calyx diameter (cm) | 4.0 | 5.0 | 4.2 |
| Average weight (gm) | 19.3 | 23.1 | 17.6 |
| Achene color | 5Y 6/8-7.5R 3/8 | 5Y 6/8-7.5R 3/8 | 5Y6/8-7.5R 3/8 |
| Achenes per berry | 254 | 304 | 293 |
| Achene weight (mg) | 0.59 | 0.61 | 0.56 |
| Marketable yield (gm/plt) | 1,219 | 1,392 | 1,010 |
| Size | Medium to small | Medium to large | Small |
| Predominant shape | Conical | Conical | Conical |
| Difference in shapes between primary and secondary fruit | None or very slight | Moderate | Slight |
| Band without achenes | Absent or very narrow | Absent or very narrow | Absent or very narrow |
| Unevenness of surface | Absent or very weak | Weak | Absent or very |
| Evenness of color | Even | Slightly uneven to even | Even |
| Glossiness | Strong | Medium to strong | Strong |
| Insertion of achenes | Level with surface | Level with surface | Level with surface |
| Insertion of calyx | In the basin to level | Level to above fruit | In the basin to level |
| Attitude of the calyx | Spreading to reflexed | Spreading to reflexed | Collapsing to reflexed |
| Size of calyx in relation to fruit diameter | Slightly larger | Slightly larger | Slightly larger |
| Adherence of calyx | Strong | Strong | Strong |
| Firmness of skin | Strong | Medium | Strong |
| Firmness of flesh | Firm | Medium | Medium to firm |
| Keeping quality: | Excellent | Moderate | Excellent |
| Distribution of red color of the flesh | Only marginal | Marginal and central | Marginal and central |
| Hollow center expression | Moderate | Moderate to strong | Moderate to strong |
| Flavor | Good | Very good | Fair |
| Soluble solids (% Brix) | 8.3 | 8.0 | 7.4 |
| Time of first flowering | Medium | Early | Late |

TABLE 2-continued

| FRUIT CHARACTERISTICS | | | |
|---|---|---|---|
| Characteristic | 'PS-5096' | 'PS-592' (U.S. Plant Pat. No. 9,903) | 'PS-1150' (U.S. Plant Pat. No. 10,780) |
| Flowering period | Early March | Late February to early March | Mid March |
| Time of first harvesting | Medium | Early | Late |
| Harvest period | Early April to early December | Late March to early December | Mid April to early December |
| Type of bearing | Partially remontant | Partially remontant | Partially remontant |

TABLE 3

| PLANT CHARACTERISTICS | | | |
|---|---|---|---|
| Characteristic | 'PS-5096' | 'PS-592' (U.S. Plant Pat. No. 9,903) | 'PS-1150' (U.S. Plant Pat. No. 10,780) |
| Height of plant (cm) | 29.7 | 31.0 | 30.0 |
| Spread of plant (cm) | 31.7 | 35.1 | 28.8 |
| Crowns/plant | 5.5 | 5.0 | 5.0 |
| Size | Large to medium | Large | Medium |
| Habit | Globose | Globose | Globose |
| Density | Medium | Open to medium | Medium |
| Vigor | Medium to strong | Strong | Medium |

TABLE 4

| STOLON CHARACTERISTICS | | | |
|---|---|---|---|
| Characteristic | 'PS-5096' | 'PS-592' (U.S. Plant Pat. No. 9,903) | 'PS-1150' (U.S. Plant Pat. No. 10,780) |
| Average stolon number per plant from the fruiting field | Few | Few to medium | Few |
| Anthocyanin coloration | 7.5R 6/6-6/4 | 7.5R 5/6-5/4 | 7.5R 4/6-5/6 |
| Anthocyanin intensity | Absent or very weak | Medium | Medium to strong |
| Diameter at bract (mm) | 4.0 | 4.4 | 4.2 |
| | Thin to medium | Thick | Thin to medium |
| Pubescence | Weak to medium | Medium | Medium to strong |

TABLE 5

| FOLIAGE CHARACTERISTICS | | | |
|---|---|---|---|
| Characteristic | 'PS-5096' | 'PS-592' (U.S. Plant Pat. No. 9,903) | 'PS-1150' (U.S. Plant Pat. No. 10,780) |
| Foliage: | | | |
| Color of upper surface | 7.5GY 4/4-3/4 Medium green | 7.5GY 4/4-3/4 Medium green | 7.5GY 4/4-3/4 Medium green |
| Color of under side | 5GY 5/4-6/4 Light to medium grey green | 5GY 5/4-6/4 Light to medium grey green | 5GY 5/4-6/4 Light to medium grey green |

TABLE 5-continued

| FOLIAGE CHARACTERISTICS | | | |
|---|---|---|---|
| Characteristic | 'PS-5096' | 'PS-592' (U.S. Plant Pat. No. 9,903) | 'PS-1150' (U.S. Plant Pat. No. 10,780) |
| Shape in cross section | Slightly concave to slightly convex | Slightly concave | Slightly concave to slightly convex |
| Interveinal blistering | Medium | Medium to strong | Weak to medium |
| Glossiness | Medium | Strong | Weak |
| Number of leaflets | 3 | 3 | 3 to 4 |
| Terminal Leaflet: | | | |
| Length (cm) | 9.2 | 9.5 | 7.2 |
| Width (cm) | 6.6 | 8.0 | 6.4 |
| Length/width ratio | 1.39 | 1.19 | 1.13 |
| Serrations/leaf | 20.7 | 20.7 | 19.3 |
| Size | Much longer than broad | Much longer than broad | Longer than broad |
| Shape of base | Acute | Acute | Obtuse |
| Shape of teeth | Obtuse | Obtuse | Obtuse |
| Petiole: | | | |
| Length (cm) | 20.8 | 21.1 | 19.0 |
| Diameter (mm) | 3.6 | 4.7 | 3.1 |
| Petiolule length (mm) | 13.0 | 15.7 | 9.3 |
| Pubescence | Moderate to sparse | Moderate to sparse | Moderate to sparse |
| Attitude of hairs | Slightly outward | Strongly outward | Strongly outward |
| Size bract leaflets | Small | Small to medium | Small |
| Stipules: | | | |
| Length (mm) | 15.4 | 20.8 | 14.5 |
| Width (mm) | 8.3 | 8.5 | 8.4 |
| Anthocyanin coloration | Medium | Medium | Absent or very weak |
| Color | Light to medium green | Light to medium green | Light to medium green |

TABLE 6

| FRUITING TRUSS CHARACTERISTICS | | | |
|---|---|---|---|
| Characteristic | 'PS-5096' | 'PS-592' (U.S. Plant Pat. No. 9,903) | 'PS-1150' (U.S. Plant Pat. No. 10,780) |
| Length at maturity (cm) | 35.5 | 37.3 | 38.1 |
| Position relative to foliage | Level with to above | Beneath to level with | Above |
| Pubescence | Weak | Medium | Medium |
| Anthocyanin intensity | Light | Light | Moderate |
| Attitude at first pick | Prostrate to erect | Prostrate to erect | Prostrate to erect |

TABLE 7

| FLOWER CHARACTERISTICS | | | |
|---|---|---|---|
| Characteristic | 'PS-5096' | 'PS-592' (U.S. Plant Pat. No. 9,903) | 'PS-1150' (U.S. Plant Pat. No. 10,780) |
| Petal color | N9.5/90.0% R to N9.25/84.2% R White | N9.5/90.0% R to N9.25/84.2% R White | N9.5/90.0% R to N9.25/84.2% R White |
| Corolla diameter (mm) | 28.0 | 30.6 | 30.5 |
| Calyx diameter (mm) | 32.0 | 38.8 | 34.0 |

TABLE 7-continued

| FLOWER CHARACTERISTICS | | | |
|---|---|---|---|
| Characteristic | 'PS-5096' | 'PS-592' (U.S. Plant Pat. No. 9,903) | 'PS-1150' (U.S. Plant Pat. No. 10,780) |
| Petal length (mm) | 11.0 | 12.1 | 12.5 |
| Petal width (mm) | 10.1 | 11.5 | 10.8 |
| Petal length/width ratio | 1.09 | 1.05 | 1.15 |
| Petals/flower | 6.0 | 6.0 | 6.2 |
| Sepal length (mm) | 12.8 | 15.7 | 13.1 |
| Sepal width (mm) | 4.8 | 6.2 | 5.4 |
| Sepal length/width ratio | 2.69 | 2.54 | 2.42 |
| Sepals/flower | 12.1 | 11.9 | 12.4 |
| Size of calyx relative to corolla | Larger | Larger | Larger |
| Size of inner calyx relative to outer calyx | Same | Smaller to same | Smaller to same |
| Relative position of petals | Overlapping | Overlapping | Overlapping |

TABLE 8

| PEST AND DISEASE REACTIONS | | | |
|---|---|---|---|
| Characteristic | 'PS-5096' | 'PS-592' (U.S. Plant Pat. No. 9,903) | 'PS-1150' (U.S. Plant Pat. No. 10,780) |
| Two spotted spider mite | Moderately susceptible | Moderately susceptible | Moderately susceptible |
| Lygus bug | Susceptible | Susceptible | Susceptible |
| Flower thrips | Moderately susceptible | Moderately susceptible | Moderately susceptible |
| Powdery mildew | Moderately susceptible | Moderately susceptible | Moderately susceptible |
| Botrytis fruit rot | Moderately susceptible | Moderately susceptible | Moderately susceptible |
| Angular leaf spot | Moderately susceptible | Moderately susceptible | Moderately susceptible |
| Virus complex | Unknown | Unknown | Unknown |

We claim:

1. A new and distinct strawberry plant named 'PS-5096', as herein described and illustrated by the characteristics set forth above.

* * * * *